United States Patent
Esch et al.

(10) Patent No.: US 9,918,897 B2
(45) Date of Patent: Mar. 20, 2018

(54) QUANTUM REFLEX INTEGRATION APPARATUS

(71) Applicants: Paul Esch, Villa Rica, GA (US); Bonnie Brandes, Crystal River, FL (US)

(72) Inventors: Paul Esch, Villa Rica, GA (US); Bonnie Brandes, Crystal River, FL (US)

( * ) Notice: Subject to any disclaimer, the term of this patent is extended or adjusted under 35 U.S.C. 154(b) by 218 days.

(21) Appl. No.: 14/897,368

(22) PCT Filed: Jun. 11, 2014

(86) PCT No.: PCT/US2014/041878
§ 371 (c)(1),
(2) Date: Dec. 10, 2015

(87) PCT Pub. No.: WO2014/201096
PCT Pub. Date: Dec. 18, 2014

(65) Prior Publication Data
US 2016/0128901 A1    May 12, 2016

Related U.S. Application Data

(60) Provisional application No. 61/833,994, filed on Jun. 12, 2013.

(51) Int. Cl.
*A61H 39/00* (2006.01)
*A61N 5/06* (2006.01)
(Continued)

(52) U.S. Cl.
CPC ............ *A61H 39/00* (2013.01); *A61N 2/002* (2013.01); *A61N 2/02* (2013.01); *A61N 5/0618* (2013.01);
(Continued)

(58) Field of Classification Search
CPC ................... A61N 5/06; A61N 5/0613; A61N 2005/0629; A61N 2005/0644;
(Continued)

(56) References Cited

U.S. PATENT DOCUMENTS 7,537,576 B1 * 5/2009 Worley, III ............ A61H 1/001
601/46
2003/0004556 A1    1/2003 McDaniel
(Continued)

FOREIGN PATENT DOCUMENTS

WO    WO2012024243 A1    2/2012
WO    WO2013036677 A1    3/2013

OTHER PUBLICATIONS

"The Symphony of Reflexes", reflexintegration.net, Products, 2015.
(Continued)

*Primary Examiner* — Thaddeus Cox
(74) *Attorney, Agent, or Firm* — Daniel M. Cohn; Howard M. Cohn

(57) ABSTRACT

Embodiments of the present invention provide an apparatus for performing quantum reflex integration. A signal generator (106) is configured and disposed to generate an output pattern (220). In embodiments, the pattern may comprise discrete frequency pulses spanning a given frequency range. In some embodiments, the frequency ranges from 1 Hz to 2000 Hz. Embodiments may further comprise a transducer (116) coupled to the signal generator (106), such that the transducer (116) outputs a response that corresponds to the output pattern (220). The transducer may include, but is not limited to, a speaker (114), and an electromagnetic coil. Embodiments may further comprise one or more cold lasers (110). In some embodiments, multiple lasers may be used. Embodiments may include lasers of different wavelengths.
(Continued)

In some embodiments, the lasers may include a red laser, a violet laser, and an infrared laser.

11 Claims, 8 Drawing Sheets

(51) Int. Cl.
*A61N 5/067* (2006.01)
*A61N 2/00* (2006.01)
*A61N 2/02* (2006.01)
*A61B 18/00* (2006.01)

(52) U.S. Cl.
CPC ............ *A61B 2018/00732* (2013.01); *A61H 2039/005* (2013.01); *A61H 2201/501* (2013.01); *A61H 2201/5015* (2013.01); *A61H 2201/5043* (2013.01); *A61N 2005/067* (2013.01); *A61N 2005/0651* (2013.01); *A61N 2005/0663* (2013.01)

(58) Field of Classification Search
CPC ...... A61N 2005/065; A61N 2005/0651; A61N 2005/0652; A61N 2005/0663; A61H 39/00; A61H 2039/005
See application file for complete search history.

(56) References Cited

U.S. PATENT DOCUMENTS

| | | | |
|---|---|---|---|
| 2006/0206174 A1* | 9/2006 | Honeycutt | A61N 2/02 607/88 |
| 2007/0248136 A1 | 10/2007 | Leonardo et al. | |
| 2007/0260296 A1* | 11/2007 | Porter | A61N 5/062 607/88 |
| 2009/0088822 A1 | 4/2009 | Pruitt et al. | |
| 2010/0121158 A1* | 5/2010 | Quevedo | A61B 5/0482 600/301 |
| 2011/0106224 A1* | 5/2011 | Kribbe | A61N 5/0613 607/91 |
| 2011/0172747 A1* | 7/2011 | Weisbart | A61N 5/0613 607/89 |
| 2011/0224584 A1 | 9/2011 | Pryor et al. | |
| 2012/0203055 A1* | 8/2012 | Pletnev | A61N 2/002 600/14 |

OTHER PUBLICATIONS

Cocilovo et al.: "New Developments in Color Therapy: Acupuncture Meridians Facilitate the Body's Absorption of Light. Explore", vol. 9, No. 2., 1999, pp. 1-6.

* cited by examiner

QUANTUM REFLEX INTEGRATION APPARATUS

TECHNICAL FIELD OF THE INVENTION

The present invention relates generally to an electronic device for signal generation, and more particularly, to an electronic device for generating signals for therapeutic applications.

BACKGROUND OF THE INVENTION

Primitive reflexes are automatic responses of infants to elements of their environment which are essential for survival. These reflexes, when integrated in the first months of growth, lead to the development of muscle tone, motor skills, sensory integration and cognition. When these primary reflexes remain active and dominant, difficulties emerge. In children who experienced birth brain injuries, these reflexes are never integrated. Additionally, reflexes which were integrated can later re-activate in cases of anoxia (near drowning), brain trauma, toxins, etc. and impede healing as they remain dominant and not integrated.

Primitive reflexes originate in the brain stem, which is the area responsible for survival. The body, under stress, acts from the brain stem and cannot access the prefrontal cortex where information is analyzed. Hence, children and adults with brain assaults can re-activate these reflexes and develop issues of a lack of mobility and function, lack of control of bodily function, speech delay etc. It is therefore desirable to have an apparatus to assist in re-integrating these reflexes to facilitate the healing process.

SUMMARY OF THE INVENTION

QRI (Quantum Reflex Integration) uses a cold laser and targets certain acupuncture or trigger points which facilitate integration of primitive reflexes. QRI benefits children and adults who have learning challenges such as ADD/ADHD, dyslexia, dysgraphia, dyscalculia, speech disorders, auditory processing disorders, dyspraxia, and visual processing disorders. Also, those with autism and Asperger's syndrome, sensory and motor disorders, traumatic brain injuries, cerebral palsy, autoimmune diseases, genetic disorders, and dementia can benefit. QRI also assists those seeking improved general health.

Embodiments of the present invention provide an apparatus for performing quantum reflex integration. A signal generator is configured and disposed to generate an output pattern. In embodiments, the pattern may comprise discrete frequency pulses spanning a given frequency range. In some embodiments, the frequency ranges from 1 Hz to 2000 Hz. Embodiments may further comprise a transducer coupled to the signal generator, such that the transducer outputs a response that corresponds to the output pattern. The transducer may include, but is not limited to, a speaker, and an electromagnetic coil. Embodiments may further comprise one or more cold lasers. In some embodiments, multiple lasers may be used. Embodiments may include lasers of different wavelengths. In some embodiments, the lasers may include a red laser, a violet laser, and an infrared laser. In some embodiments, the lasers may output light at one or more of the following wavelengths: 650 nanometers, 780 nanometers, and/or 405 nanometers.

Embodiments may further comprise one or more light emitting diodes (LEDs). In embodiments, the light emitting diodes may operate synchronously with the lasers. Embodiments may comprise light emitting diodes which produce light of different colors. In some embodiments, the LED colors may include red, orange, yellow, green, blue, indigo, violet, and white. Alternatively, another suitable light source, such as small incandescent bulbs, may be used in place of, or in addition to, the light emitting diodes. In some embodiments, a particular LED may be activated based on a given frequency range of the output pattern. The output pattern may comprise a frequency sweep which outputs a sine wave starting at 1 Hz, and gradually increasing to 2000 Hz over a predetermined sweep time interval. In other embodiments, another wave type may be used in place of a sine wave, including, but not limited to, a square wave, and a sawtooth wave. In some embodiments, the output is an on/off duty cycle of one or more lasers. For example, at 10 Hz, the lasers may be turning on and off at 10 times per second. In some embodiments, the sweep time interval ranges from 10 seconds to 60 seconds. A processor may be configured and disposed to activate one or more of a plurality of lasers and LEDs in a synchronized manner. In some embodiments, the red LED may be activated for frequencies ranging from 1 Hz to 250 Hz. In some embodiments, the orange LED may be activated for frequencies ranging from 251 Hz to 500 Hz. In some embodiments, the yellow LED may be activated for frequencies ranging from 501 Hz to 750 Hz. In some embodiments, the green LED may be activated for frequencies ranging from 751 Hz to 1000 Hz. In some embodiments, the blue LED may be activated for frequencies ranging from 1001 Hz to 1250 Hz. In some embodiments, the indigo LED may be activated for frequencies ranging from 1251 Hz to 1500 Hz. In some embodiments, the violet LED may be activated for frequencies ranging from 1501 Hz to 1750 Hz. In some embodiments, the white LED may be activated for frequencies ranging from 1751 Hz to 2000 Hz.

Embodiments may further comprise an expansion port. The expansion port facilitates connecting another device to the apparatus, such as an additional transducer. In some embodiments, the expansion port facilitates connecting multiple apparatuses together in a master-slave configuration.

One aspect of the present invention provides an apparatus comprising: a processor; memory containing instructions executable by the processor; a signal generator configured to generate an output pattern; a speaker configured to output a sound or tone corresponding to the output pattern; a plurality of lasers configured to output a light modulated by the output pattern; and a plurality of light emitting diodes configured to output a light modulated by the output pattern.

In another aspect, embodiments of the present invention provide an apparatus for performing quantum reflex integration, comprising: a signal generator; a memory; a processor configured and disposed to access the memory; a laser bank comprising a plurality of lasers; a plurality of light emitting diodes (LEDs); wherein the processor is configured and disposed to activate one or more of the plurality of lasers and LEDs in a synchronized manner.

In another aspect, embodiments of the present invention provide a system for performing quantum reflex integration, comprising a first apparatus and a second apparatus, wherein each apparatus comprises: a signal generator; a memory; a processor configured and disposed to access the memory; a laser bank comprising a plurality of lasers; a plurality of light emitting diodes (LEDs); and an expansion port; wherein the processor is configured and disposed to activate one or more of the plurality of lasers and LEDs in a synchronized manner; and wherein the first apparatus is configured as a master apparatus, and wherein the second apparatus is configured as a slave apparatus, and wherein the expansion port of the first apparatus is coupled to the expansion port of the second apparatus.

In another aspect, embodiments of the present invention provide an apparatus for performing quantum reflex integration, comprising: a signal generator; a memory; a processor configured and disposed to access the memory; a laser bank comprising a plurality of lasers; a plurality of light emitting diodes (LEDs); wherein the processor is configured and disposed to activate one or more of the plurality of lasers and LEDs in a synchronized manner; a user interface comprising a report feature, wherein the processor is configured to output a usage report from the apparatus upon activation of the report feature.

BRIEF DESCRIPTION OF THE DRAWINGS

The structure, operation, and advantages of the present invention will become further apparent upon consideration of the following description taken in conjunction with the accompanying figures (FIGs.). The figures are intended to be illustrative, not limiting.

Certain elements in some of the figures may be omitted, or illustrated not-to-scale, for illustrative clarity. The cross-sectional views may be in the form of "slices", or "near-sighted" cross-sectional views, omitting certain background lines which would otherwise be visible in a "true" cross-sectional view, for illustrative clarity.

Figure 1A:
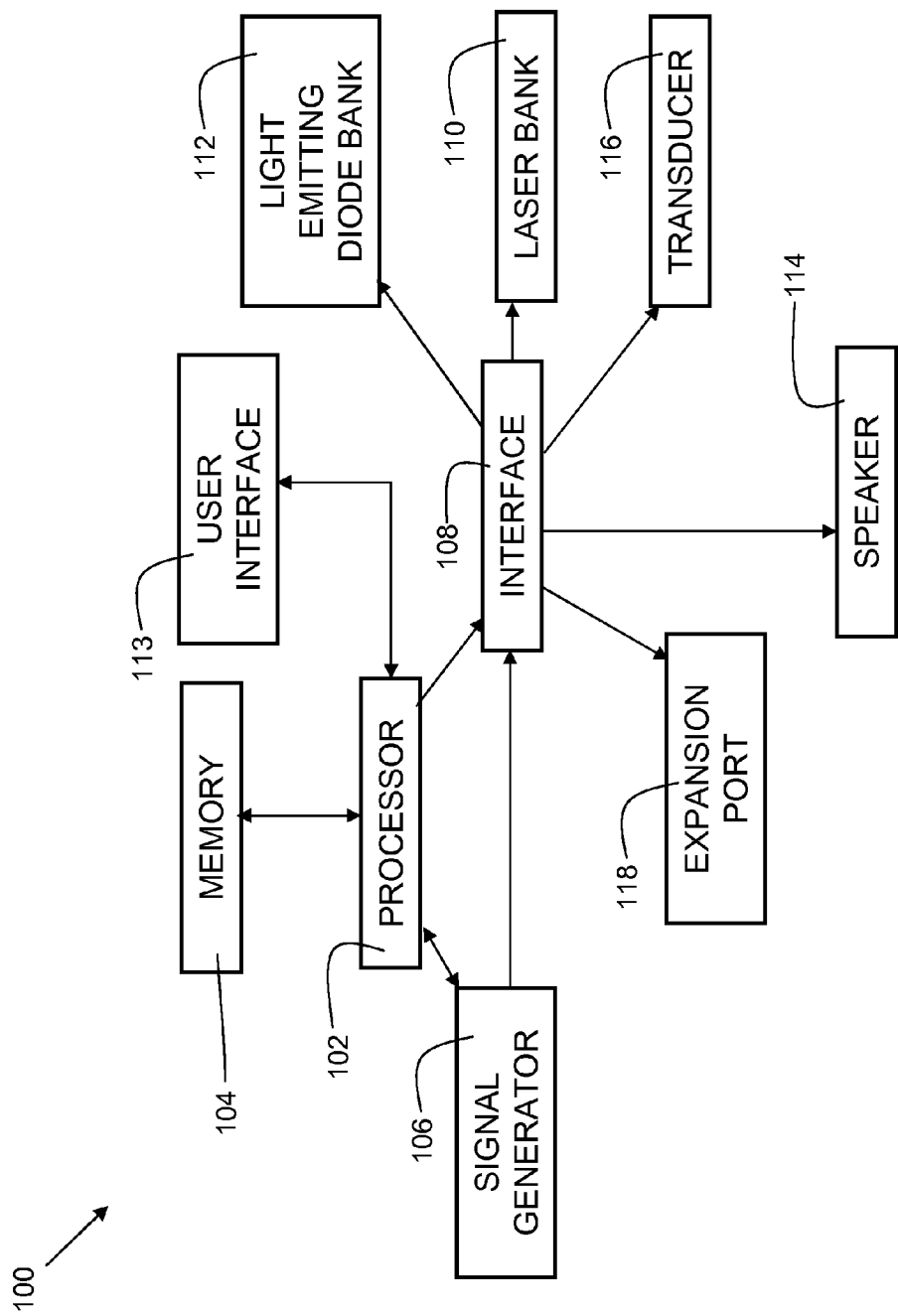

Often, similar elements may be referred to by similar numbers in various figures (FIGs) of the drawing, in which case typically the last two significant digits may be the same, the most significant digit being the number of the drawing figure (FIG). Furthermore, for clarity, some reference numbers may be omitted in certain drawings.

FIG. 1A is a block diagram of an apparatus in accordance with embodiments of the present invention.

Figure 1B:
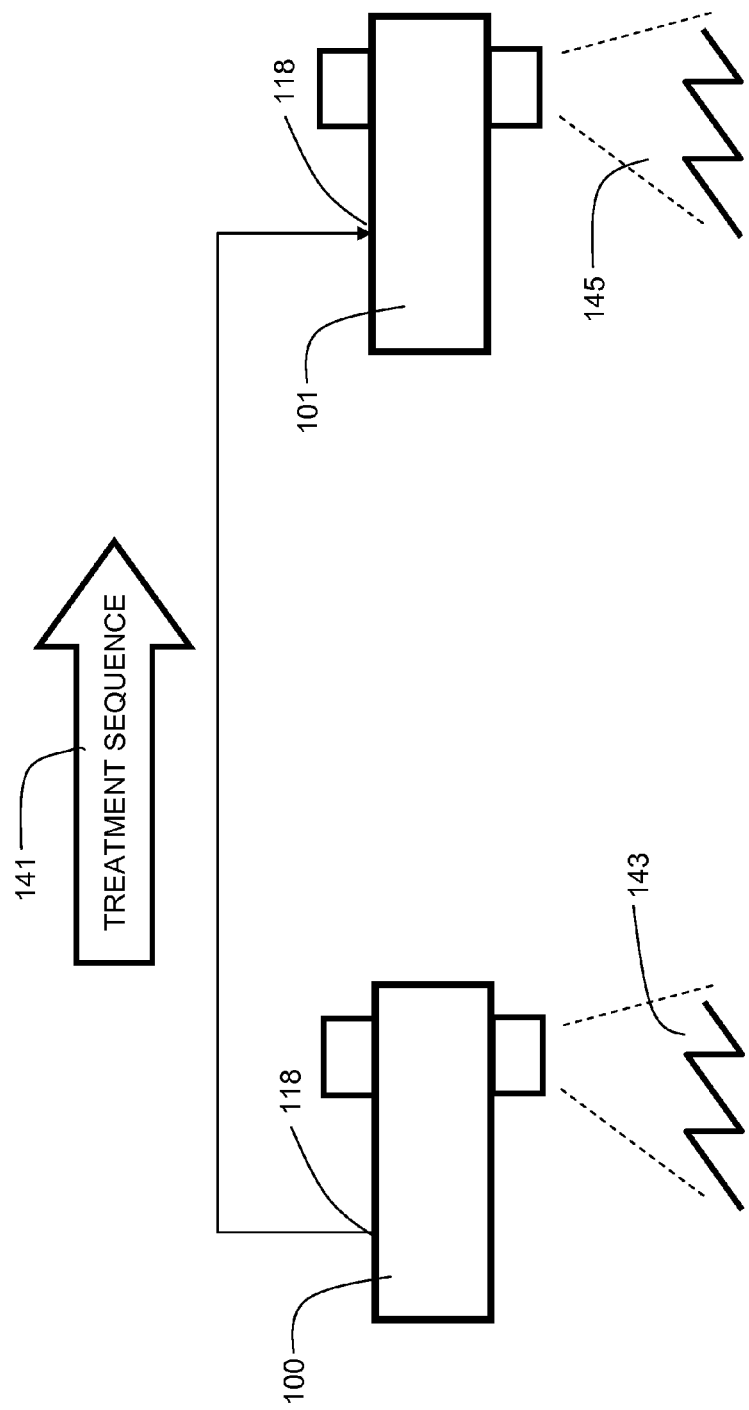

FIG. 1B is an exemplary embodiment showing a master-slave configuration.

Figure 2:
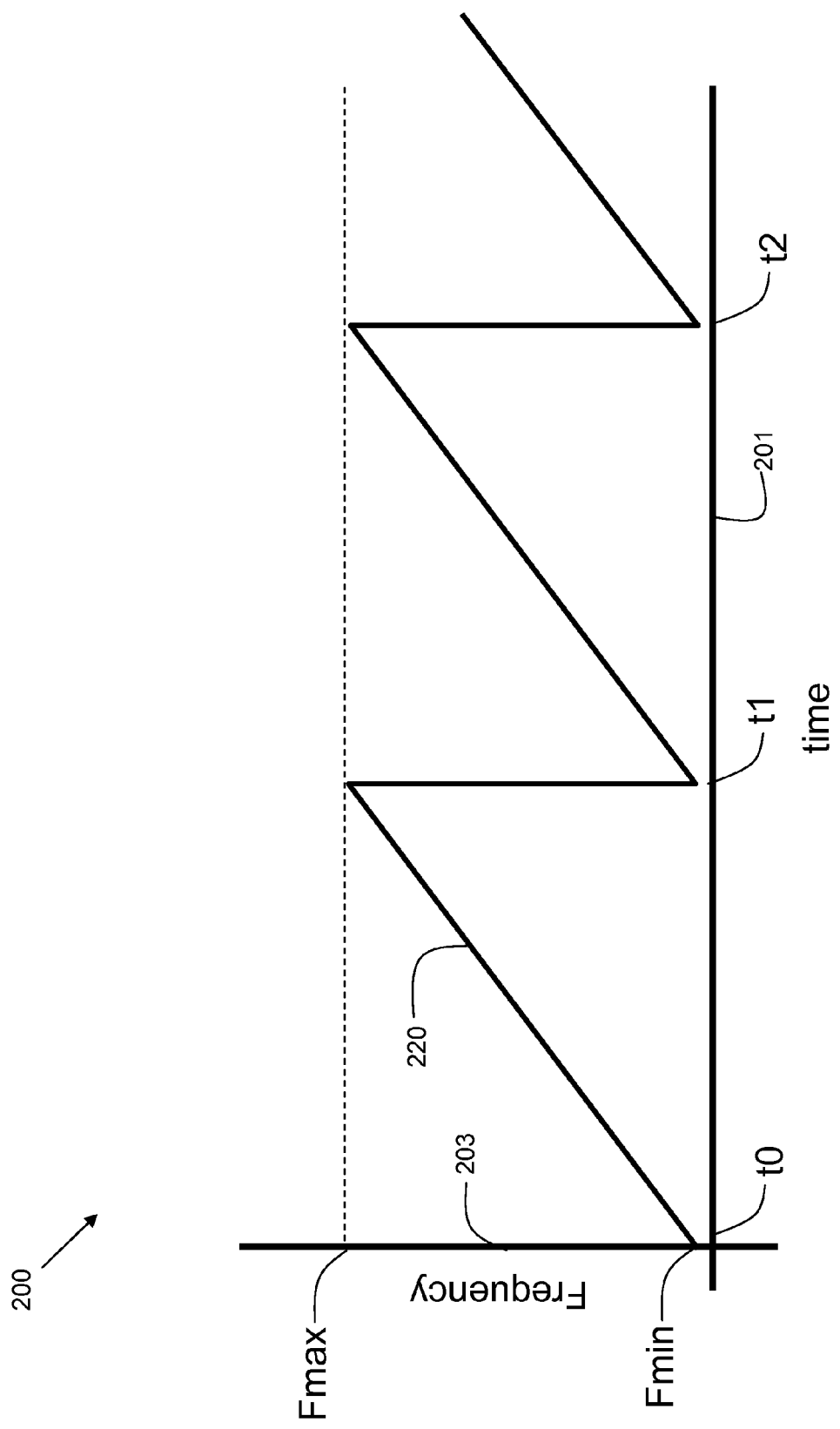

FIG. 2 is an output pattern in accordance with embodiments of the present invention.

Figure 3:
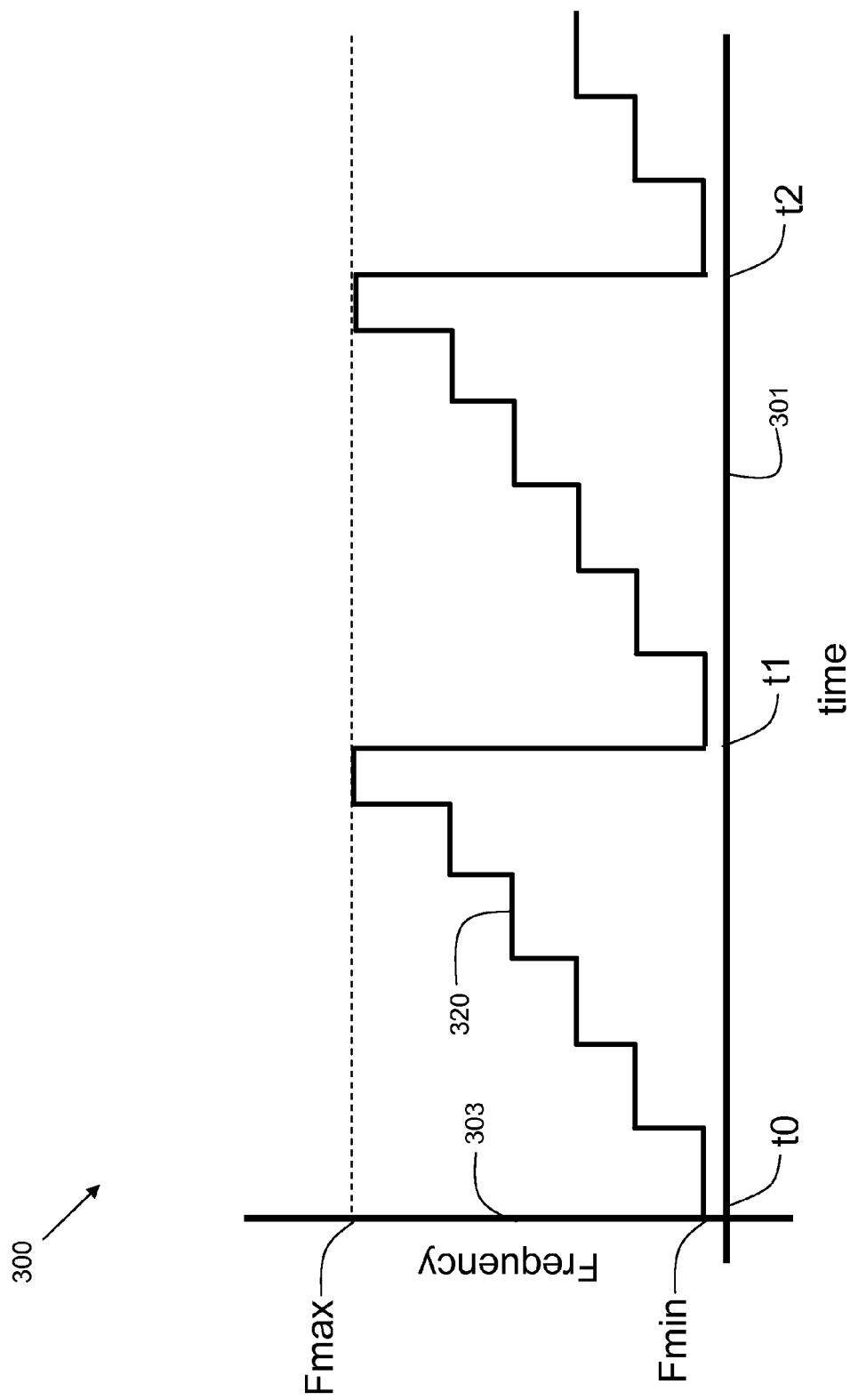

FIG. 3 is an output pattern in accordance with alternative embodiments of the present invention.

Figure 4A:
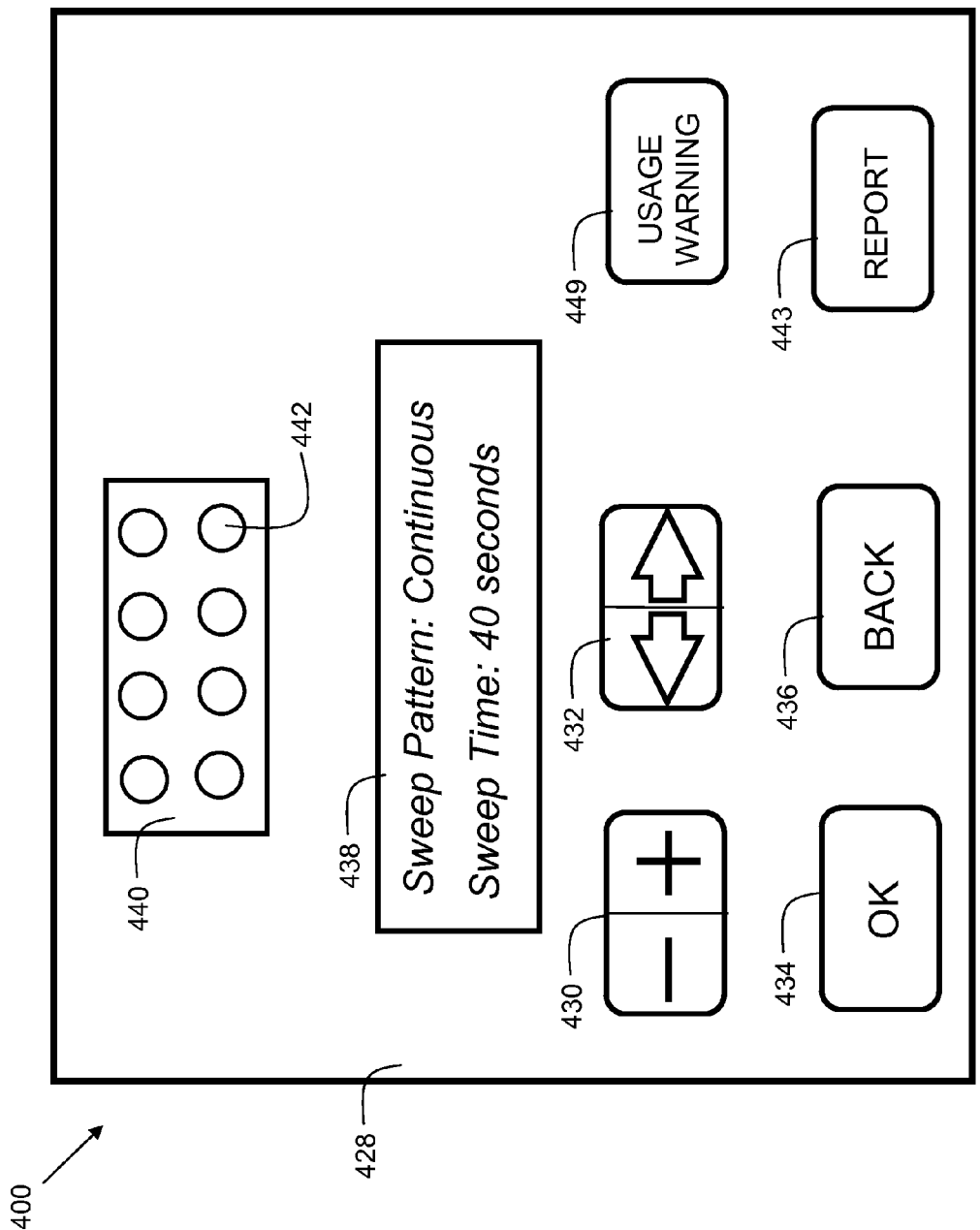

FIG. 4A is a top-down view of an embodiment of the present invention.

Figure 4B:
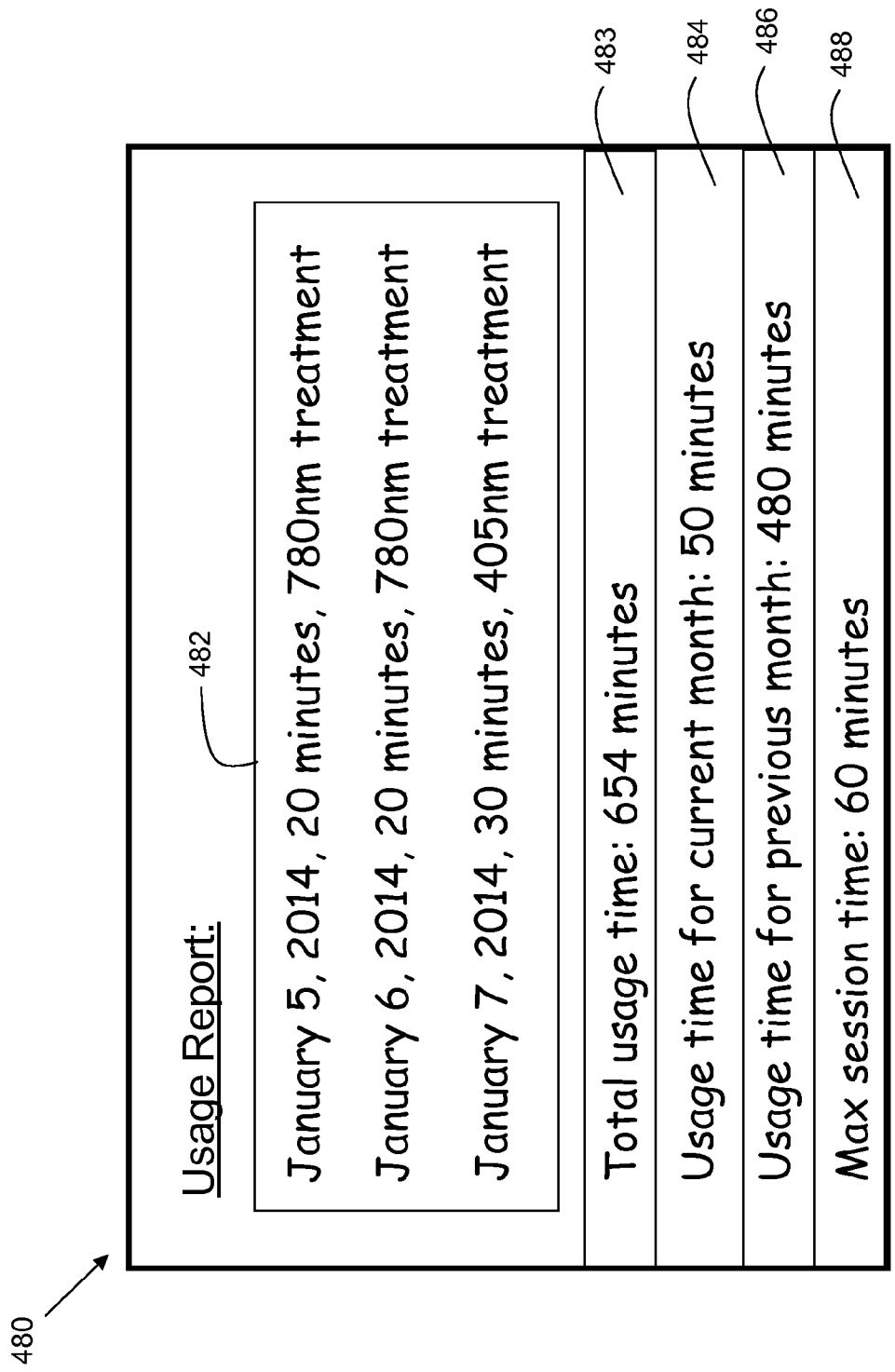

FIG. 4B is an exemplary usage report in accordance with embodiments of the present invention.

Figure 5:
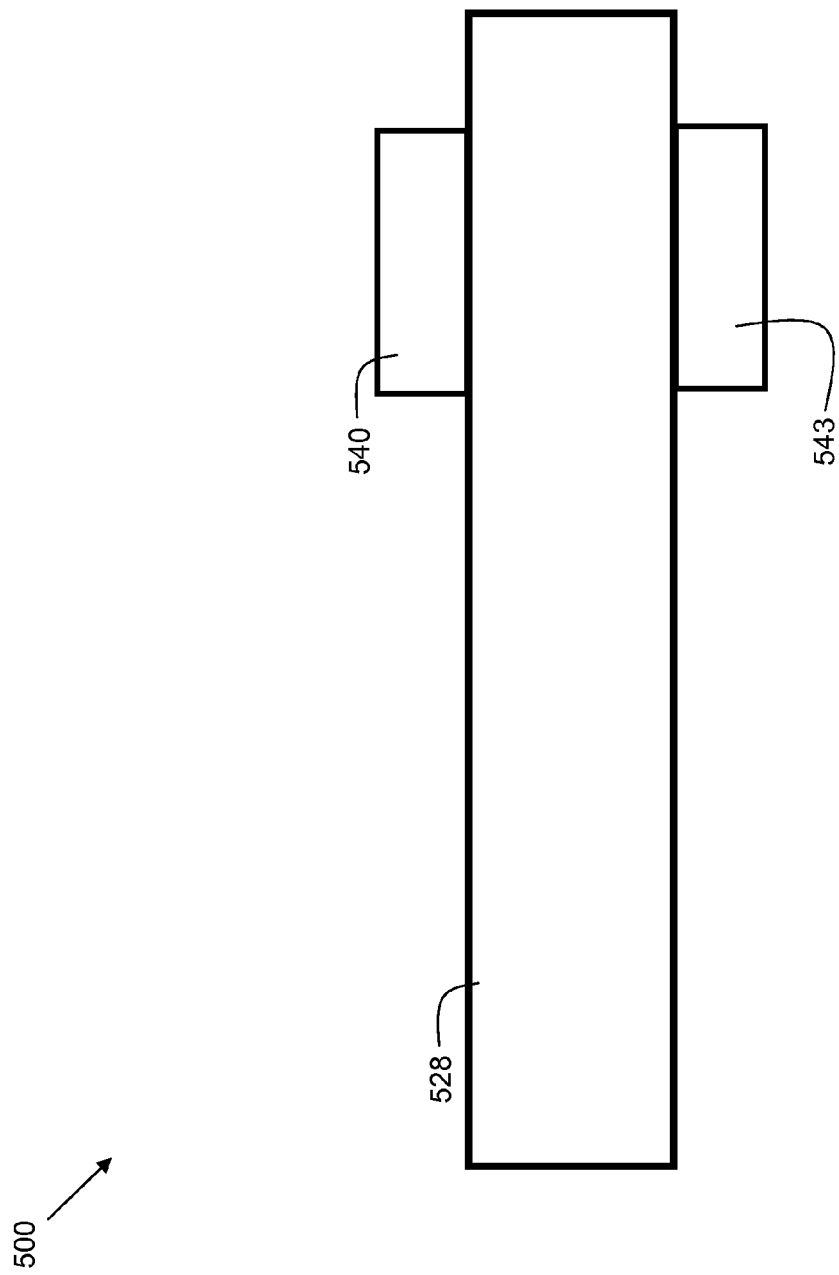

FIG. 5 is a side view of an embodiment of the present invention.

Figure 6:
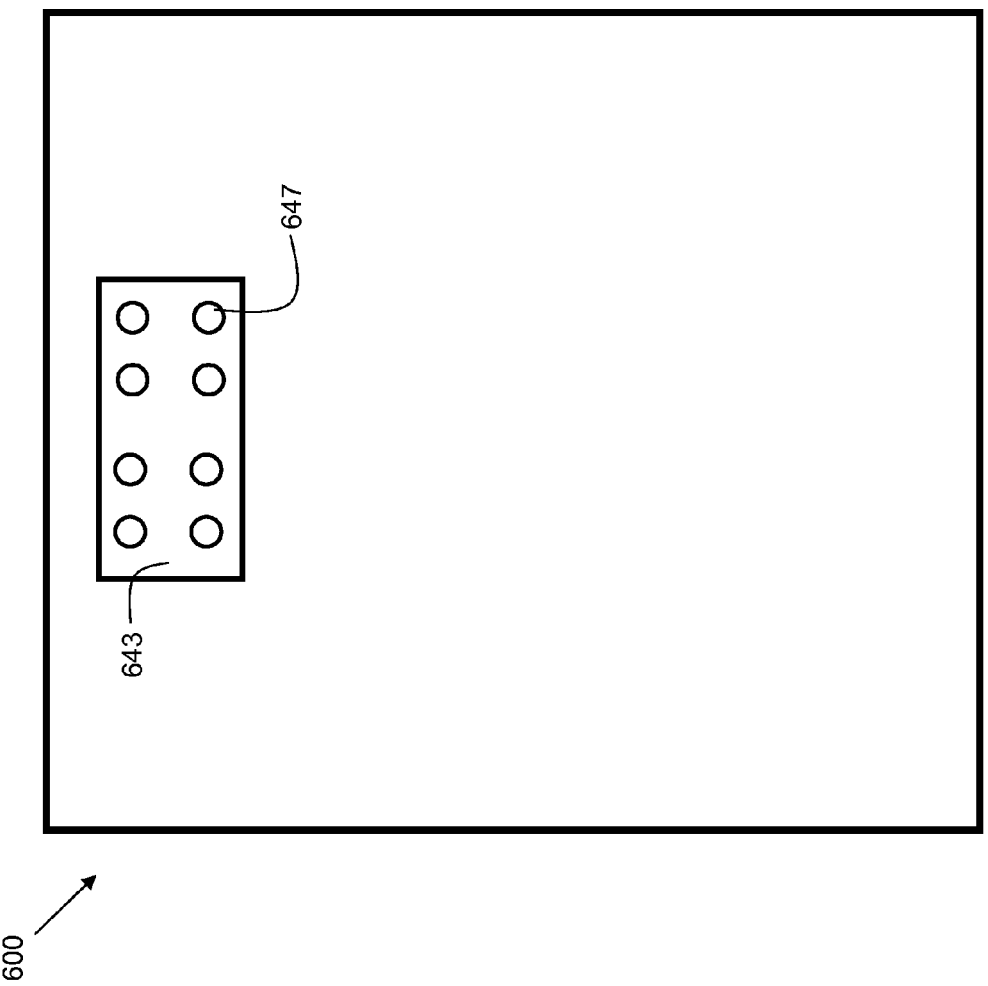

FIG. 6 is a bottom-up view of an embodiment of the present invention.

DETAILED DESCRIPTION

FIG. 1A is a block diagram of an apparatus 100 in accordance with embodiments of the present invention. A processor 102 is configured to access memory 104 which contains instructions that when executed by processor 102, control the various functions of apparatus 100. Memory 104 may comprise a non-transitory memory, and may include a hard disk, a random access memory (RAM), a read-only memory (ROM), an erasable programmable read-only memory (EPROM, Flash, MRAM, FeRAM, or phase change memory), a memory card, a portable compact disc read-only memory (CD-ROM), an optical storage device, a magnetic storage device, or any suitable combination of the foregoing. A variety of languages for expressing computer program instructions may include without limitation C, C++, Java, JavaScript, assembly language, Lisp, Perl, Tcl, Python, Ruby, hardware description languages, database programming languages, functional programming languages, imperative programming languages, and so on.

Apparatus 100 comprises a signal generator 106. The signal generator 106 may be configured by processor 102 for various modes of operation. In some embodiments, a sweep pattern is output from the signal generator 106. The sweep pattern may comprise an electronic signal in the form of a sine wave output, with a gradual increase from a minimum frequency to a maximum frequency over a sweep period time. In embodiments, the minimum frequency may be 1 hertz and the maximum frequency may be 2000 Hertz. In embodiments, the sweep period time may range from 10 seconds to about 100 seconds.

The signal generator 106 outputs an electronic signal to interface 108. Interface 108 comprises circuitry for conditioning the output of signal generator 106 to drive various types of output devices. Output devices may include, but are not limited to, a light emitting diode (LED) bank 112. The LED bank 112 may include one or more LEDs. The LEDs may be configured to display various colors. This may be achieved by using a different colored plastic shroud for each LED. In some embodiments, the LED colors include, but are not limited to, red, orange, yellow, green, blue, indigo, violet, and white. In addition to, or instead of, LEDs, an alternative light source, such as small incandescent bulbs may be used.

Embodiments may include, but are not limited to, a laser (LED) bank 110. The laser bank 110 may include one or more cold lasers. The cold lasers may be configured to display various colors. In some embodiments, the lasers emit light at the following wavelengths: 650 nanometers, 780 nanometers, and/or 405 nanometers. In embodiments, the cold lasers have a power output ranging from about 50 milliwatts to about 150 milliwatts.

Embodiments may include, but are not limited to, a speaker 114. The speaker 114 may output a sine wave with the same frequency as the output pattern of signal generator 106. Embodiments may further include a transducer 116. The transducer 116 may be an electromagnetic coil which is configured and disposed to output electromagnetic energy corresponding to the output of signal generator 106. In embodiments, the electromagnetic coil is configured to a produce magnetic field that is synchronized to a laser output pattern.

Embodiments may further include an expansion port 118. The expansion port 118 may include, but is not limited to, an analog audio output jack, such as a headphone type jack (e.g. ⅛ inch stereo or mono jack) that facilitates connecting external speakers or headphones to hear the sound. In other embodiments, the expansion port 118 may include a USB port and/or a wireless interface. In embodiments, the wireless interface may include a near-field communication interface such as Bluetooth, for communication with a nearby mobile device such as a tablet computer or mobile phone.

In an embodiment with a Bluetooth interface, the apparatus 100 may communicate with a program ("app") that is executing on a tablet computer. The tablet computer may provide an interface for controlling the parameters of the apparatus 100. In addition, the apparatus 100 may synchronize operation to a playlist of music that is played from the tablet computer during a treatment session. For example, the sweep pattern frequency may be slower while a slower song is playing, and then the sweep pattern frequency may increase when a subsequent, faster tempo song is playing.

In another embodiment, as illustrated in FIG. 1B, the expansion port 118 may be used to couple the apparatus 100 to another apparatus 101 in a master-slave configuration. In the master-slave configuration, a first apparatus is programmed with a desired treatment sequence. The treatment sequence includes a setting of lasers, light emitting diodes, and/or sounds. The first apparatus serves as a master, and the second apparatus 101 is configured as a slave apparatus. The treatment sequence 141 is then sent from the first (master) apparatus 100 to the second (slave) apparatus 101. In embodiments, the first apparatus sends the treatment sequence as a series of commands to the second apparatus to control the operation of the second apparatus. For example, the first apparatus may send a command to activate one or more lasers at a sweep pattern for a desired duration. In this way, both apparatuses 100 and 101 operate in unison in a synchronized manner, with apparatus 100 generating output 143, and apparatus 101 generating output 145. For example, in such a configuration, the user may perform a laser treatment on the left knee and right knee simultaneously using both apparatuses in a master-slave configuration. In some embodiments, the output 143 and 145 may be identical. In other embodiments, the outputs 143 and 145 may be different. For example, the master apparatus 100 and slave apparatus 101 may operate in an alternating manner.

Embodiments may further include a user interface 113. The user interface 113 may comprise a screen and a plurality of buttons. Some embodiments may include a keypad. Some embodiments may include a touch screen. The user interface 113 may be configured to display various parameters to the user, such as the current output pattern and frequency. The user interface 113 may also provide a mechanism for controlling or adjusting various parameters, including, but not limited to, speaker volume, sweep time interval, and output pattern. Other embodiments may include establishing a fixed frequency (e.g. 440 Hertz) instead of a changing pattern.

FIG. 2 is a graph 200 showing an output pattern 220 in accordance with embodiments of the present invention. The horizontal axis 201 represents time. The vertical axis 203 represents frequency of a wave over time. The output pattern 220 starts at a frequency Fmin at time t0, and includes a continuous increase in frequency up to a maximum frequency Fmax at time t1. The process then repeats, up until time t2. The difference between time t1 and time t0 represents the sweep time interval. In some embodiments, the sweep time interval may range from 10 seconds to 100 seconds. In some embodiments, Fmin is 1 Hz and Fmax is 2000 Hz.

FIG. 3 is a graph 300 showing an output pattern 320 in accordance with alternative embodiments of the present invention. The horizontal axis 301 represents time. The vertical axis 303 represents frequency of a wave over time. The output pattern 320 starts at a frequency Fmin at time t0, and includes a stepped increase in frequency up to a maximum frequency Fmax at time t1. While six stepped levels per sweep are shown in FIG. 3, some embodiments may have 8 stepped levels or more. In one embodiment, a first level has a fundamental frequency of 250 Hz, a second level has a fundamental frequency of 500 Hz, a third level has a fundamental frequency of 750 Hz, a fourth level has a fundamental frequency of 1000 Hz, a fifth level has a fundamental frequency of 1250 Hz, a sixth level has a fundamental frequency of 1500 Hz, a seventh level has a fundamental frequency of 1750 Hz, and an eighth level has a fundamental frequency of 2000 Hz. The process then repeats, up until time t2. The difference between time t1 and time t0 represents the sweep time interval.

FIG. 4A is a top-down view of an apparatus 400 in accordance embodiment of the present invention. Apparatus 400 may be used to perform QRI (Quantum Reflex Integration). Apparatus 400 comprises an enclosure 428. Within the enclosure 428 is a display 438. Display 438 may be a liquid crystal display (LCD) or other suitable display. Apparatus 400 may further comprise navigation control 432, volume control 430, an OK button 434, and a BACK button 436. The navigation control 432, OK button 434, volume control 430, and BACK button 436 may be used to navigate menus displayed on display 438 and allow user configuration of various parameters such as pattern selection (continuous as in FIG. 2 or stepped as in FIG. 3), sweep time interval, or setting a fixed frequency output (e.g. 440 Hz). The volume of the sound may also be adjusted. Some embodiments may have a touch screen, and all buttons may be "soft" buttons that are rendered on the touch screen. Optionally, the apparatus 400 may further comprise a report feature 443. The report feature 443 may be implemented by a button, that is configured such that when pressed, causes a usage report to be sent from apparatus 400 to a computer (or tablet or mobile phone) via the expansion port 118, USB port, or wireless (Bluetooth) interface. As shown in FIG. 4B, the report 480 may include a recent activity log 482, indicating recent usage durations, dates, and the parameters (such as treatment wavelength) used during the user session. Additionally, a total usage time for the lifetime of the device may be displayed in field 483. A usage time for the current month may be shown in field 484. A usage time for the previous month may be shown in field 486. A maximum session time setting may be shown in field 488. The maximum session time may be entered by a user using navigation control 432 and display 438. This feature serves to prevent overuse of the device. If the current session exceeds the maximum usage time, the usage warning indication 449 (see FIG. 4A) may be illuminated. Optionally, an audio alert may be provided. In some embodiments, the lasers may be deactivated upon exceeding the maximum usage time. The lasers may remain in a deactivated state for a predetermined period or until a reset operation (e.g. a power cycling of the apparatus) is performed.

Apparatus 400 may be powered by a battery (not shown). In some embodiments, the battery may be a rechargeable battery. Other embodiments may utilize non-rechargeable batteries. Other embodiments may utilize AC power instead of, or in addition to battery power. An LED bank 440 may include one or more light emitting diodes, indicated generally as reference 442. Some embodiments may comprise eight LEDs. The LEDs may comprise a variety of colors. Some embodiments may include an infrared LED. Some embodiments may include LEDs of one or more of the following colors: red, orange, yellow, green, blue, indigo, violet, and white.

FIG. 5 is a side view of an apparatus 500 in accordance with an embodiment of the present invention. Apparatus 500 comprises enclosure 528. LED bank 540 is disposed on the top of the enclosure 528. Laser bank 543 is disposed on the bottom of the enclosure 528.

FIG. 6 is a bottom-up view of an apparatus 600 in accordance with an embodiment of the present invention. Apparatus 600 comprises laser bank 643, which may include one or more lasers, indicated generally as reference 647. Lasers 647 may be cold lasers. The cold lasers may be configured to display various colors. In some embodiments, the lasers emit the following wavelengths: 650 nanometers, 780 nanometers, and/or 405 nanometers. In some embodiments, the lasers may be equipped with a frosted diffuser that helps protect the eyes from harm. Some embodiments may include lasers that provide pulsed laser light. Some embodiments may also include lasers that provide a continuous beam. Some embodiments may include lasers that provide a wavelength between 600 nm and 720 nm. Other embodiments may include lasers that provide a wavelength between 760 nm and 905 nm. Other embodiments may include lasers that provide a wavelength between 405 nm and 420 nm.

The application of laser light over injuries, lesions, burns, wounds, pain, inflammation and other disorders to stimulate healing within those tissues and cells. Low level lasers, under various names such as, cold lasers, may serve as therapeutic energy devices to bring about favorable biological effects in both humans and animals.

Laser irradiation of tissue cultures has shown that units of light energy (photons) are absorbed by enzymes, which react to light within the cell. Visible red light is absorbed within the mitochondria and the infrared light is absorbed at the cell membrane.

In a mammalian cell, this results in a change in membrane permeability, increased ATP levels and increased DNA production. ATP is an abbreviation for adenosine triphosphate, a complex molecule that contains the nucleoside adenosine and a tail consisting of three phosphates. The photons picked up by the cell membrane result in improved membrane stability and increased activity of the ATP dependent Na/K pump. Because cell metabolism is influenced by Na/K movement across the membrane, increasing the gradient will affect the flow of ions and hence the overall metabolism of the cell.

On a tissue level, irradiation by laser light results in increased collagen and epithelial production and production of new capillaries and an increase in density of the capillary bed.

There are 75 trillion cells in a human body and they all need electrons to communicate with each other. Laser light delivers required electrons and photons (little energy packets) directly to the cells and enhances both their ability to communicate with each other and their ability to produce ATP (chemical energy), which they require for optimal functioning. Additionally laser light causes the release of anti-inflammatory enzymes and the production of endorphins, which are natural pain-killers and mood elevators.

As can now be appreciated, embodiments of the present invention provide an apparatus for performing quantum reflex integration. A signal generator is configured to modulate one or more lasers. Sound corresponding to the output of the signal generator may also be presented. Light emitting diodes (LEDs) corresponding to the output of the signal generator may also be presented.

Although the invention has been shown and described with respect to a certain preferred embodiment or embodiments, certain equivalent alterations and modifications will occur to others skilled in the art upon the reading and understanding of this specification and the annexed drawings. In particular regard to the various functions performed by the above described components (assemblies, devices, circuits, etc.) the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

What is claimed is:

1. An apparatus for performing quantum reflex integration, comprising:
a signal generator; a memory; a processor configured and disposed to access the memory;
a laser bank comprising a plurality of lasers; a plurality of light emitting diodes (LEDs); wherein the processor is configured and disposed to activate one or more of the plurality of lasers and LEDs in a synchronized manner; and wherein the plurality of LEDs comprises a red LED, an orange LED, a yellow LED, a blue LED, a green LED, a white LED, an indigo LED, and a violet LED, and, wherein the processor is configured and disposed to: activate the red LED in response to an output frequency ranging from 1 Hz to 250 Hz; activate the orange LED in response to an output frequency ranging from 251 Hz to 500 Hz; activate the yellow LED in response to an output frequency ranging from 501 Hz to 750 Hz; activate the green LED in response to an output frequency ranging from 751 Hz to 1000 Hz; activate the blue LED in response to an output frequency ranging from 1001 Hz to 1250 Hz; activate the indigo LED in response to an output frequency ranging from 1251 Hz to 1500 Hz; activate the violet LED in response to an output frequency ranging from 1501 Hz to 1750 Hz; and activate the white LED in response to an output frequency ranging from 1751 Hz to 2000 Hz.

2. The apparatus of claim 1, wherein the apparatus further comprises a speaker, wherein the speaker is configured to produce a tone corresponding to a laser output pattern.

3. The apparatus of claim 1, further comprising an expansion port.

4. The apparatus of claim 3, wherein the expansion port comprises a USB port.

5. The apparatus of claim 3, wherein the expansion port comprises a Bluetooth interface.

6. The apparatus of claim 1, wherein the apparatus further comprises an electromagnetic coil, wherein the electromagnetic coil is configured to produce a magnetic field that is synchronized to a laser output pattern.

7. The apparatus of claim 1, wherein the plurality of lasers comprises: a first laser configured to emit light at a wavelength of 650 nanometers; a second laser configured to emit light at a wavelength of 780 nanometers; and a third laser configured to emit light at a wavelength of 405 nanometers.

8. A system for performing quantum reflex integration, comprising a first apparatus and a second apparatus, wherein each apparatus comprises: a signal generator; a memory; a processor configured and disposed to access the memory; a laser bank comprising a plurality of lasers; a plurality of light emitting diodes (LEDs); and an expansion port; wherein the processor is configured and disposed to activate one or more of the plurality of lasers and LEDs in a synchronized manner; and wherein the first apparatus is configured as a master, and wherein the second apparatus is configured as a slave, and wherein the expansion port of the first apparatus is coupled to the expansion port of the second apparatus; and, wherein the plurality of LEDs of each apparatus comprises a red LED, an orange LED, a yellow LED, a blue LED, a green LED, a white LED, an indigo LED, and a violet LED; and wherein the processor of each apparatus is configured and disposed to: activate the red LED in response to an output frequency ranging from 1 Hz to 250 Hz; activate the orange LED in response to an output frequency ranging from 251 Hz to 500 Hz; activate the yellow LED in response to an output frequency ranging from 501 Hz to 750 Hz; activate the green LED in response to an output frequency ranging from 751 Hz to 1000 Hz; activate the blue LED in response to an output frequency ranging from 1001 Hz to 1250 Hz; activate the indigo LED in response to an output frequency ranging from 1251 Hz to 1500 Hz; activate the violet LED in response to an output frequency ranging from 1501 Hz to 1750 Hz; and activate the white LED in response to an output frequency ranging from 1751 Hz to 2000 Hz.

9. The system of claim 8, wherein the first apparatus is configured and disposed to send a treatment sequence to the second apparatus.

10. The system of claim 9, wherein the treatment sequence includes a command to activate one or more lasers at a sweep pattern for a desired duration.

11. The system of claim 8, wherein the plurality of lasers of each apparatus comprises: a first laser configured to emit light at a wavelength of 650 nanometers; a second laser configured to emit light at a wavelength of 780 nanometers; and a third laser configured to emit light at a wavelength of 405 nanometers.

* * * * *